United States Patent
Zhao et al.

(10) Patent No.: US 11,517,610 B2
(45) Date of Patent: Dec. 6, 2022

(54) BONE REPAIR MATERIAL AND PREPARATION METHOD THEREOF, AND BIOLOGICAL COMPOSITE SCAFFOLD

(71) Applicant: BOE TECHNOLOGY GROUP CO., LTD., Beijing (CN)

(72) Inventors: Tianxiao Zhao, Beijing (CN); Zhichao Li, Beijing (CN); Changjun Liu, Beijing (CN); Xianzhen Li, Beijing (CN); Tianyue Zhao, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 233 days.

(21) Appl. No.: 16/639,193

(22) PCT Filed: Jun. 21, 2019

(86) PCT No.: PCT/CN2019/092376
§ 371 (c)(1),
(2) Date: Feb. 14, 2020

(87) PCT Pub. No.: WO2020/042733
PCT Pub. Date: Mar. 5, 2020

(65) Prior Publication Data
US 2021/0128686 A1    May 6, 2021

(30) Foreign Application Priority Data
Aug. 31, 2018 (CN) .......................... 201811014216.8

(51) Int. Cl.
*A61K 38/18* (2006.01)
*A61K 47/69* (2017.01)
*A61K 47/52* (2017.01)
*A61K 9/00* (2006.01)
*A61K 38/06* (2006.01)
*A61K 38/10* (2006.01)
*A61K 38/39* (2006.01)
*A61K 47/02* (2006.01)
*A61K 47/34* (2017.01)
*A61K 47/42* (2017.01)

(52) U.S. Cl.
CPC ........ *A61K 38/1875* (2013.01); *A61K 9/0024* (2013.01); *A61K 38/06* (2013.01); *A61K 38/10* (2013.01); *A61K 38/39* (2013.01); *A61K 47/02* (2013.01); *A61K 47/34* (2013.01); *A61K 47/42* (2013.01); *A61K 47/52* (2017.08); *A61K 47/6953* (2017.08)

(58) Field of Classification Search
None
See application file for complete search history.

(56) References Cited

U.S. PATENT DOCUMENTS

| | | | |
|---|---|---|---|
| 9,402,710 B2 * | 8/2016 | Yang | A61L 27/225 |
| 2009/0087493 A1 * | 4/2009 | Dai | A61K 9/0092 |
| | | | 424/490 |
| 2010/0075904 A1 * | 3/2010 | Laurencin | A61P 19/08 |
| | | | 977/752 |

FOREIGN PATENT DOCUMENTS

| | | | | |
|---|---|---|---|---|
| CN | 102552932 | | 7/2012 | |
| CN | 104857569 | | 8/2015 | |
| CN | 105079806 | | 11/2015 | |
| CN | 105079806 A | * | 11/2015 | |
| CN | 106860916 | | 6/2017 | |
| CN | 106860916 A | * | 6/2017 | ........... A61L 27/443 |
| CN | 107362389 | | 11/2017 | |
| CN | 107537063 | | 1/2018 | |
| CN | 108126207 | | 6/2018 | |
| CN | 108421085 | | 8/2018 | |
| WO | 2003088925 | | 10/2003 | |
| WO | 2011049719 | | 4/2011 | |

OTHER PUBLICATIONS

Fu, Scientific Reports, 7, 12549, 2017 (Year: 2017).*
Zhang, Nanotechnol Rev, 2, 1,2013 (Year: 2013).*
Development and Research of New Medicine, Dec. 31, 2008; pp. 1078-1079.
Chinese Office Action dated Dec. 3, 2019 corresponding to Chinese Patent Application No. 201811014216.8; 19 pages.

* cited by examiner

*Primary Examiner* — Robert A Wax
*Assistant Examiner* — William Craigo
(74) *Attorney, Agent, or Firm* — Leason Ellis LLP

(57) ABSTRACT

A bone repair material, a preparation method of the bone repair material, and a biological composite scaffold are provided. The bone repair material includes: a base material, and a carbon nanomaterial and a polypeptide both mixed with the base material; and the carbon nanomaterial and the polypeptide are bonded by chemical bonds. The preparation method includes: bonding a carbon nanomaterial with a polypeptide by chemical bonds; and mixing the carbon nanomaterial and the polypeptide bonded by the chemical bonds with a base material, and performing a molding treatment.

17 Claims, 4 Drawing Sheets

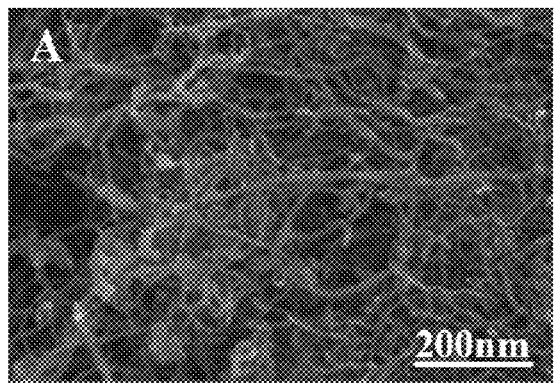
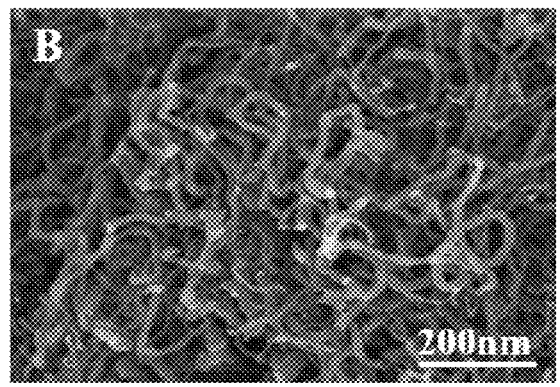
FIG. 3A　　　　　　　　　　　FIG. 3B
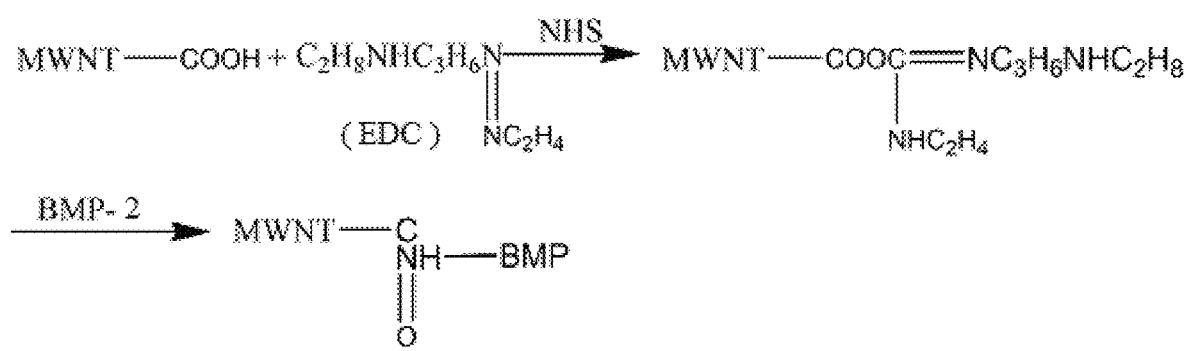
FIG. 4

BONE REPAIR MATERIAL AND PREPARATION METHOD THEREOF, AND BIOLOGICAL COMPOSITE SCAFFOLD

CROSS-REFERENCE TO RELATED PATENT APPLICATIONS

This application is a U.S. National Stage Application under 35 U.S.C. § 371 of International Patent Application No. PCT/CN2019/092376, filed Jun. 21, 2019, which claims priority of Chinese Patent Application No. 201811014216.8 filed on Aug. 31, 2018, both of which are incorporated herein by reference in their entireties as part of the present disclosure.

TECHNICAL FIELD

Embodiments of the present disclosure relate to a bone repair material, a preparation method of the bone repair material, and a biological composite scaffold.

BACKGROUND

Bone defect caused by disease or trauma is always a big problem to be solved in the orthopaedic field. At present, commonly used bone repair methods in clinic include an autogenous bone transplantation method or an allogeneic bone transplantation method, but both the autogenous bone transplantation method and the allogeneic bone transplantation method have some limitations. For example, the autogenous bone transplantation method is difficult to meet the requirements due to limited donors. The allogeneic bone transplantation method often fails due to the immune rejection of human body, and sometimes the transplanted bone carries virus, thus causes disease.

SUMMARY

At least one embodiment of the present disclosure provides a bone repair material, and the bone repair material comprises: a base material, and a carbon nanomaterial and a polypeptide both mixed with the base material; and the carbon nanomaterial and the polypeptide are bonded by chemical bonds.

For example, in the bone repair material provided by at least one embodiment of the present disclosure, the polypeptide comprises one or more selected from a group consisting of BMP-2 polypeptide, BMP-7 polypeptide, BMP-9 polypeptide, RGD polypeptide, OGP osteogenic polypeptide, and OPN polypeptide.

For example, in the bone repair material provided by at least one embodiment of the present disclosure, the base material comprises one or more selected from a group consisting of hydroxyapatite, tricalcium phosphate, and bioglass.

For example, in the bone repair material provided by at least one embodiment of the present disclosure, the carbon nanomaterial comprises one or more selected from a group consisting of carbon nanotube, graphene, and graphene oxide.

For example, in the bone repair material provided by at least one embodiment of the present disclosure, the carbon nanotube is a multiple-walled carbon nanotube.

For example, the bone repair material provided by at least one embodiment of the present disclosure, further comprises a polymer molding material.

For example, in the bone repair material provided by at least one embodiment of the present disclosure, the polymer molding material comprises one or more selected from a group consisting of polylactic acid, polycaprolactone, poly (lactic-co-glycolic acid), polyglycolic acid and collagen.

For example, in the bone repair material provided by at least one embodiment of the present disclosure, the polylactic acid comprises poly(L-lactic acid) having a molecular weight in a range of 20000 to 40000.

For example, in the bone repair material provided by at least one embodiment of the present disclosure, a total mass fraction of the bone repair material is 100 parts, a mass fraction of the base material ranges from 15 parts to 30 parts; a mass fraction of the carbon nanomaterial ranges from 6 parts to 10 parts; a mass fraction of the polypeptide ranges from 3 parts to 5 parts; and a mass fraction of the polymer molding material ranges from 50 parts to 70 parts.

At least one embodiment of the present disclosure further provides a preparation method of a bone repair material, and the preparation method comprises: bonding a carbon nanomaterial with a polypeptide by chemical bonds; mixing the carbon nanomaterial and the polypeptide bonded by the chemical bonds with a base material.

For example, the preparation method of the bone repair material provided by at least one embodiment of the present disclosure, further comprises: performing a molding treatment on the carbon nanomaterial, the polypeptide, and the base material that have been mixed.

For example, in the preparation method of the bone repair material provided by at least one embodiment of the present disclosure, mixing the carbon nanomaterial and the polypeptide bonded by the chemical bonds with the base material and performing the molding treatment comprise: mixing the base material with a polymer molding material to form a first mixed solution, mixing the carbon nanomaterial and the polypeptide bonded by the chemical bonds with the first mixed solution to form a second mixed solution, and performing the molding treatment on the second mixed solution.

For example, in the preparation method of the bone repair material provided by at least one embodiment of the present disclosure, a solvent for preparing the first mixed solution comprises one or more selected from a group consisting of 1,4-dioxane, dichloromethane and trichloromethane.

For example, in the preparation method of the bone repair material provided by at least one embodiment of the present disclosure, bonding the carbon nanomaterial with the polypeptide by the chemical bonds further comprises: performing a carboxylation treatment on the carbon nanomaterial, and mixing the carbon nanomaterial performed with the carboxylation treatment with the polypeptide, so as to allow the carbon nanomaterial to be bonded with the polypeptide by the chemical bonds.

For example, in the preparation method of the bone repair material provided by at least one embodiment of the present disclosure, the carboxylation treatment is an acidification treatment.

For example, in the preparation method of the bone repair material provided by at least one embodiment of the present disclosure, an acid used for the acidification treatment comprises one or more selected from a group consisting of sulfuric acid, nitric acid and hydrogen peroxide.

For example, in the preparation method of the bone repair material provided by at least one embodiment of the present disclosure, bonding the carbon nanomaterial with the polypeptide by the chemical bonds further comprises: performing an activation treatment on the carbon nanomaterial performed with the carboxylation treatment to activate a carboxyl group of the carbon nanomaterial, and mixing the carbon nanomaterial performed with the activation treatment with the polypeptide, so as to allow the carbon nanomaterial to be bonded with the polypeptide by the chemical bonds.

For example, in the preparation method of the bone repair material provided by at least one embodiment of the present disclosure, the activation treatment uses a solution including 1-ethyl-(3-dimethylaminopropyl) carbodiimide hydrochloride.

For example, in the preparation method of the bone repair material provided by at least one embodiment of the present disclosure, bonding the carbon nanomaterial with the polypeptide by the chemical bonds further comprises: performing a stabilization treatment on the carbon nanomaterial performed with the activation treatment to convert the carboxyl group into an ester group, and mixing the carbon nanomaterial performed with the stabilization treatment with the polypeptide, so as to allow the carbon nanomaterial to be bonded with the polypeptide by the chemical bonds.

For example, in the preparation method of the bone repair material provided by at least one embodiment of the present disclosure, the stabilization treatment uses a solution including N-hydroxysuccinimide.

For example, in the preparation method of the bone repair material provided by at least one embodiment of the present disclosure, the molding treatment is performed by a freeze-drying method.

At least one embodiment of the present disclosure further provides a biological composite scaffold, and the biological composite scaffold comprises any one of the bone repair material mentioned above.

BRIEF DESCRIPTION OF THE DRAWINGS

In order to clearly illustrate the technical solution of the embodiments of the present disclosure, the drawings of the embodiments will be briefly described. It is apparent that the described drawings are only related to some embodiments of the present disclosure and thus are not limitative of the present disclosure.

FIG. 3A is a scanning electron micrograph of a carbon nanomaterial before a carboxylation treatment provided by at least one embodiment of the present disclosure;

FIG. 3B is a scanning electron micrograph of a carbon nanomaterial after the carboxylation treatment provided by at least one embodiment of the present disclosure;

FIG. 4 is a schematic diagram illustrating a carbon nanomaterial being bonded with a polypeptide by chemical bonds provided by at least one embodiment of the present disclosure;

DETAILED DESCRIPTION

Figure 1:
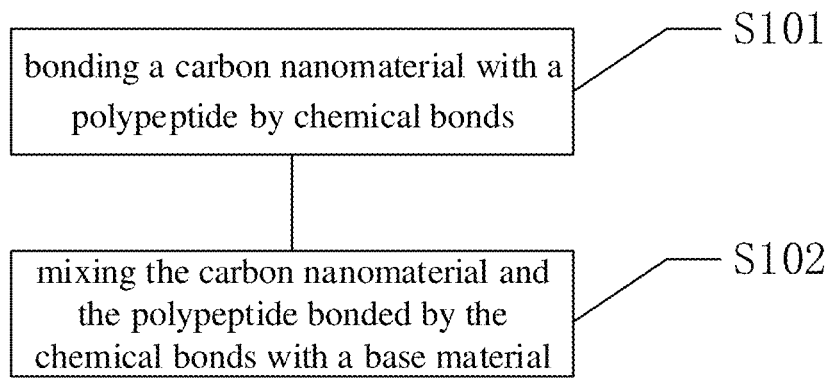
FIG. 1 is a flow chart of a preparation method of a bone repair material provided by at least one embodiment of the present disclosure.

In order to make objects, technical details and advantages of embodiments of the present disclosure clear, the technical solutions of the embodiments will be described in a clearly and fully understandable way in connection with the related drawings. It is apparent that the described embodiments are just a part but not all of the embodiments of the present disclosure. Based on the described embodiments herein, those skilled in the art can obtain, without any inventive work, other embodiment(s) which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and claims of the present disclosure, are not intended to indicate any sequence, amount or importance, but distinguish various components. The terms "comprises," "comprising," "includes," "including," etc., are intended to specify that the elements or the objects stated before these terms encompass the elements or the objects listed after these terms as well as equivalents thereof, but do not exclude other elements or objects. The phrases "connect", "connected", etc., are not intended to define a physical connection or a mechanical connection, but may comprise an electrical connection which is direct or indirect. The terms "on," "under," "right," "left" and the like are only used to indicate relative position relationship, and in a case that the position of an object is described as being changed, the relative position relationship may be changed accordingly.

Bone repair materials used in the orthopedic field usually need to have a certain mechanical property, biocompatibility and bone repair ability. However, the properties of the bone repair materials with different compositions are quite different, the current bone repair materials are often difficult to meet the comprehensive requirements of clinic for their mechanical properties and the bone repair ability at the same time. In addition, in the current bone repair materials, the compositions of the bone repair materials are only combined by mechanical mixing, and it is difficult to form a strong binding force between various compositions. Therefore, some compositions with pharmacological functions are often released quickly, which makes the bone repair materials unable to maintain long-term activity.

At least one embodiment of the present disclosure provides a bone repair material, and the bone repair material comprises: a base material, and a carbon nanomaterial and a polypeptide both mixed with the base material; and the carbon nanomaterial and the polypeptide are bonded by chemical bonds.

At least one embodiment of the present disclosure further provides a preparation method of a bone repair material, and the preparation method comprises: bonding a carbon nanomaterial with a polypeptide by chemical bonds; mixing the carbon nanomaterial and the polypeptide bonded by the chemical bonds with a base material, and performing a molding treatment.

The bone repair material and the preparation method of the bone repair material provided by the present disclosure will be described in the following by several specific embodiments.

At least one embodiment of the present disclosure provides a bone repair material, and the bone repair material comprises: a base material, a carbon nanomaterial and a polypeptide. For example, the polypeptide has functions of osteogenic induction, promoting the growth of bone cells, and so on. Both the carbon nanomaterial and the polypeptide are mixed with the base material; and the carbon nanomaterial and the polypeptide are bonded by chemical bonds.

For example, in at least one embodiment, the base material comprises one or more selected from the group consisting of hydroxyapatite, tricalcium phosphate, and bioglass. The base material is a main chemical component of human bone, or the chemical component of the base material is similar to that of the human bone, so the base material has a good biocompatibility.

For example, in at least one embodiment, the carbon nanomaterial comprises one or more selected from the group consisting of carbon nanotube, graphene, and graphene oxide. The carbon nanomaterial promotes the adhesion and growth of osteoblasts, so as to enhance the osteogenic ability of the bone repair materials. For example, the carbon nanotube comprises a multiple-walled carbon nanotube (MWNT).

For example, in at least one embodiment, the polypeptide comprises one or more selected from the group consisting of BMP-2 polypeptide, BMP-7 polypeptide, BMP-9 polypeptide, RGD polypeptide, OGP osteogenic polypeptide, and OPN polypeptide. For example, the polypeptide has a certain osteogenic induction ability, which can further improve the biological activity and the osteogenic ability of the bone repair materials.

In the embodiments of the present disclosure, the carbon nanomaterial and the polypeptide are bonded by the chemical bonds, because the strong binding ability of the chemical bond, the polypeptide is released slowly, so that the action time of the polypeptide is prolonged and the activity of the bone repair material keeps for a long time.

For example, in an embodiment, the carbon nanomaterial is chemically modified to allow the atomic skeleton of the carbon nanomaterial to be connected with reactive functional groups. For example, the atomic skeleton of the carbon nanomaterial is connected with a plurality of carboxyl groups or ester groups, and so on. In this case, the functional groups on a polypeptide molecular chain, such as amino groups can interact with the carboxyl groups or the ester groups to form amide bonds, thus the carbon nanomaterial is bonded with the polypeptide by the amide bonds. For example, in other embodiments, the carbon nanomaterial can also be chemically modified to allow the atomic skeleton of the carbon nanomaterial to be connected with other active functional groups, so that the carbon nanomaterial is bonded with the polypeptide by different chemical bonds, which are not limited in the embodiments of the present disclosure.

For example, in an embodiment, the carbon nanomaterial uses a carbon nanotube, such as a multiple-walled carbon nanotube. The multiple-walled carbon nanotube provides more binding sites with the polypeptide, which makes the binding force between the carbon nanomaterial and the polypeptide stronger.

For example, the bone repair material provided by at least one embodiment of the present disclosure may further comprise a polymer molding material. The polymer molding material is helpful for the molding of the bone repair material and can allow the bone repair material to form a required shape. For example, the polymer molding material comprises one or more selected from the group consisting of polylactic acid, polycaprolactone, poly(lactic-co-glycolic acid), polyglycolic acid and collagen.

For example, in an embodiment, the polymer molding material is polylactic acid. For example, the polylactic acid is poly(L-lactic acid) having a molecular weight in a range of 20000 to 40000. The poly(L-lactic acid) is easy to be molded and can provide a certain mechanical ability, and the poly(L-lactic acid) is cheap and has a wide range of sources. In addition, the poly(L-lactic acid) is biodegradable, and its degradation product is lactic acid, which is one of the normal metabolites of the human body. Therefore, as a polymer molding material, the poly(L-lactic acid) has no toxic and side effects.

For example, in at least one embodiment, a mass fraction of the base material ranges from 15 parts to 30 parts, for example, 20 parts, 25 parts and so on; a mass fraction of the carbon nanomaterial ranges from 6 parts to 10 parts, for example, 7 parts, 8 parts and so on; a mass fraction of the polypeptide ranges from 3 parts to 5 parts, for example, 4 parts, 5 parts and so on; and a mass fraction of the polymer molding material ranges from 50 parts to 70 parts, for example, 55 parts, 60 parts or 65 parts and so on. In the embodiments, the fraction of each material refers to the parts of each material component in a total mass fraction of the bone repair material with 100 parts. For example, in an example, in a total mass fraction of the bone repair material with 100 parts, a mass fraction of the base material is 20 parts; a mass fraction of the carbon nanomaterial is 10 parts; a mass fraction of the polypeptide is 5 parts; and a mass fraction of the polymer molding material is 65 parts. For example, in another example, in a total mass fraction of the bone repair material with 100 parts, a mass fraction of the base material is 27 parts; a mass fraction of the carbon nanomaterial is 9 parts; a mass fraction of the polypeptide is 4 parts; and a mass fraction of the polymer molding material is 60 parts. In the above ratio, the bone repair material has a better comprehensive ability, such as a better osteogenic ability, a better mechanical property, a better molding ability and a better biocompatibility. In the embodiments, the parts of each component can also be selected according to requirements of an actual application situation, such as the requirements of an application environment for the pharmacological function or the mechanical property of the bone repair material and so on, which are not limited in the embodiments.

At least one embodiment of the present disclosure further provides a preparation method of a bone repair material, and the bone repair material comprises: a base material, a carbon nanomaterial and a polypeptide. For example, the polypeptide is a polypeptide with the osteogenic induction ability or other pharmacological functions; the preparation method can bond the carbon nanomaterial with the polypeptide by chemical bonds. For example, as illustrated in FIG. 1, the preparation method comprises step S101 and step S102.

Step S101: bonding a carbon nanomaterial with a polypeptide by chemical bonds.

Step S102: mixing the carbon nanomaterial and the polypeptide bonded by the chemical bonds with a base material.

In at least one embodiment, firstly, the carbon nanomaterial is chemically modified so that active functional groups are on the atomic skeleton of the carbon nanomaterial, which is conducive to the chemical reaction between the carbon nanomaterial and the polypeptide, so that the carbon nanomaterial and the polypeptide are bonded by the chemical bonds. For example, in an embodiment, a carboxy group or an ester group is connected to the atomic skeleton of the carbon nanomaterial by chemical modification, thus, an amide bond is formed by the interaction of the amino group on the polypeptide molecular chain with the carboxyl group or the ester group, so as to bond the carbon nanomaterial with the polypeptide by the amide bond.

For example, after mixing the carbon nanomaterial and the polypeptide bonded by the chemical bonds with the base material, a molding treatment may be performed on the carbon nanomaterial, the polypeptide, and the base material that have been mixed.

In the following, a process of bonding the carbon nanomaterial with the polypeptide is introduced by taking the carboxyl group or the ester group being connected to the atomic skeleton of the carbon nanomaterial as an example. For example, in the following example, the carbon nanomaterial is a multiple-walled carbon nanotube, the polypeptide is BMP-2 polypeptide, and the base material is hydroxyapatite. It should be noted that, in the embodiments of the present disclosure, the materials are not limited to the above materials.

Figure 2:
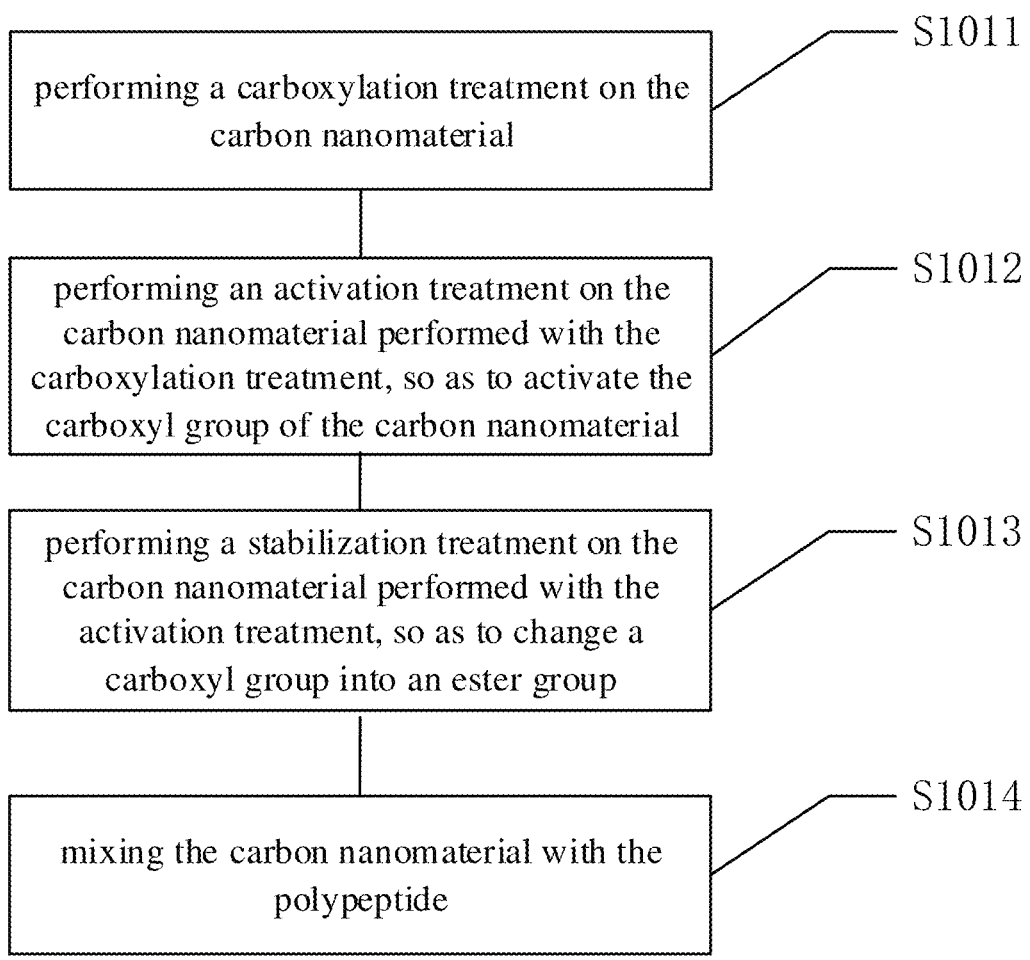
FIG. 2 is a flow chart of another preparation method of a bone repair material provided by at least one embodiment of the present disclosure.

For example, in the present example, as illustrated in FIG. 2, bonding the carbon nanomaterial with the polypeptide by the chemical bonds comprises step S1011 to step S1014.

Step S1011: performing a carboxylation treatment on the carbon nanomaterial.

In the step, performing the carboxylation treatment on the carbon nanomaterial can connect the carboxyl group with the atomic skeleton of the carbon nanomaterial. The carbon nanomaterial connected with the carboxyl group is more likely to react with the polypeptide, so as to be bonded with the polypeptide by the chemical bonds.

For example, the carboxylation treatment is an acidification treatment performed on the carbon nanomaterial. For example, an acid used for the acidification treatment comprises one or more selected from the group consisting of sulfuric acid, nitric acid and hydrogen peroxide.

For example, in an example, the carbon nanomaterial uses the carbon nanotube, for example, the multiple-walled carbon nanotube (MWNT). The specific operation of performing the carboxylation treatment on the carbon nanotube is as follows.

For example, before performing the carboxylation treatment on the carbon nanotube, performing a purification treatment on the carbon nanotube to remove the possible impurities in the carbon nanotube.

For example, the purification treatment comprises: calcining the carbon nanotube in a calciner (such as a muffle furnace), for example, calcining the carbon nanotube at a high temperature of 500° C. for 60 to 90 minutes to remove combustible impurities from the carbon nanotube. Then placing the carbon nanotube in an acidic solution, such as 6 mol/L dilute hydrochloric acid, to remove acid soluble impurities from the carbon nanotube. For example, in other embodiments, the acid solution can also be potassium permanganate solution, nitric acid solution or a mixed solution of potassium permanganate and sulfuric acid and so on, which is not limited in the embodiments of the present disclosure. For example, in a case that the carbon nanotube is placed in an acid solution, the carbon nanotube can be treated by ultrasound at the same time, for example, the ultrasound lasts for 4 hours to 5 hours to make the impurity removal more sufficient. For example, after removing the impurities, the acid solution including the carbon nanotube can be filtered and cleaned in a suction filtration device with a negative pressure of about 20 Pa until the filtrate becomes neutral. For example, the pH of the filtrate is about 6 to 7, and then the carbon nanotube is placed in a vacuum drying oven for 36 hours to 60 hours to dry the carbon nanotube.

For example, after performing the purification treatment on the carbon nanotube, a carboxylation treatment is performed on the carbon nanotube. For example, the carboxylation treatment is the acidification treatment. For example, the acid used for the acidification treatment comprises one or more selected from the group consisting of sulfuric acid, nitric acid and hydrogen peroxide. For example, in an example, the acidification treatment comprises: dissolving the carbon nanotube in a mixed solution of hydrogen peroxide and concentrated sulfuric acid with a volume ratio of 1:4, and stirring, for example, continuously stirring the mixed solution for 3 hours to 5 hours to make the carbon nanotube be completely dissolved, then placing the mixed solution in a dialysis bag, for example, for 4 days to 5 days to complete the acidification treatment. The dialysis bag allows small molecules to pass through, and the macromolecules of the carbon nanotubes do not separate out, which is beneficial to the exchange of small molecules in the dialysis bag.

For example, after the carboxylation treatment, dialysis products in the dialysis bag may be cleaned. For example, the dialysis products are repeatedly filtered and cleaned by a suction filtration method until the filtrate becomes neutral. For example, the pH of the filtrate is about 6 to 7. After that, the washed dialysis products are dried in a vacuum drying oven for 60 hours to 70 hours, so as to obtain the dried carbon nanotube connected with the carboxyl group.

FIG. 3A is a scanning electron micrograph of carbon nanotubes before a carboxylation treatment provided by at least one embodiment of the present disclosure, and FIG. 3B is a scanning electron micrograph of carbon nanotubes after the carboxylation treatment provided by at least one embodiment of the present disclosure. As illustrated in FIG. 3A, before the carboxylation treatment, an average length of the carbon nanotubes is longer and the carbon nanotubes are easy to agglomerate due to van der waals force. As illustrated in FIG. 3B, after the carboxylation treatment, the average length of the carbon nanotubes is relatively short, and the length distribution is relatively scattered, and ends of some carbon nanotubes have changed from a closed state to an open state. In a case that performing the carboxylation treatment on the carbon nanotube by the acidification treatment, the acid reacts with the carbon nanotube, and the chemical reaction, for example, occurs at the defect sites of the carbon nanotube, for example, it occurs at the end of the atomic skeleton of the carbon nanotube and a portion of the side wall of the carbon nanotube, in this case, the carboxyl group is connected to the end of the atomic skeleton of the carbon nanotube and the portion of the side wall of the carbon nanotube, and the atomic skeleton of the carbon nanotube is opened and no longer agglomerates.

The carboxylated carbon nanotube may react directly with the polypeptide, so that they can be bound by chemical bonds, or the carboxylated carbon nanotube may also be treated with other methods to enhance the reactivity of the carbon nanotube. For example, the carboxylated carbon nanotube may be activated as follows.

Step S1012: performing an activation treatment on the carbon nanomaterial performed with the carboxylation treatment.

In the step, the carboxyl group of the carbon nanomaterial can be activated by performing an activation treatment on the carbon nanomaterial, so that the carbon nanomaterial can have a higher reactivity. The activated carbon nanomaterial is easier to be mixed with the polypeptide, so that the carbon nanomaterial and the polypeptide are bonded by the chemical bonds.

For example, the activation treatment is carried out by using a solution including 1-ethyl-(3-dimethylaminopropyl) carbodiimide hydrochloride (EDC), for example, a solution including the EDC solution or a mixed solution of EDC, mercaptoacetyltriglycine, and N-hydroxysuccinimide (S-NHS) is used.

For example, in an example, the carboxylated carbon nanotube is added to the EDC solution of 5 mg/ml to 7 mg/ml, and the mixed solution is shaken for 20 minutes to 50 minutes to activate the carboxyl group on the atomic skeleton of the carbon nanotube. For example, the EDC solution is prepared by MES (2-(N-morpholino) ethanesulfonic acid) buffer solution, which is not limited in the embodiments of the present disclosure.

For example, the carbon nanotube performed with the activation treatment directly reacts with the polypeptide, so that the activated carbon nanotube and the polypeptide are bonded by the chemical bonds, or the carbon nanotube performed with the activation treatment may also be treated by other processes, for example, the activated carbon nanotube is performed with a stabilization treatment as follows to improve the stability of the functional groups used for the reaction.

Step S1013: performing a stabilization treatment on the carbon nanomaterial performed with the activation treatment.

In the step, for example, the stabilization treatment changes the carboxyl group in the carbon nanomaterial into the ester group. In a case that the carbon nanomaterial performed with the stabilization treatment reacts with the polypeptide, the reaction product is more stable and the reaction efficiency is higher.

For example, the stabilization treatment is performed by using a solution including N-hydroxysuccinimide (NHS), such as NHS solution or a mixture solution of NHS and dicyclohexylcarbodiimide (DCC) and so on.

For example, in an example, the activated carbon nanotube is added to the NHS solution of 7 mg/ml to 9 mg/ml, and the mixed solution is shaken for 20 minutes to 50 minutes to change the carboxyl group on the atomic skeleton of the carbon nanotube into the ester group. The ester group is more stable, so the active functional groups of the stabilized carbon nanotube for the reaction are more stable, and are not easy to be destroyed in the process of treatment, so the stabilized carbon nanotube has more functional groups to react with the polypeptide, furthermore, a binding force between the carbon nanotube and the polypeptide is increased, and the yield is increased. In addition, the reaction products of the stabilized carbon nanotube and the polypeptide are more stable and the reaction products can be discharged through normal metabolism of human body. For example, in the example, the NHS solution is prepared by MES (2-(N-morpholino) ethanesulfonic acid) buffer solution, which is not limited in the embodiments of the present disclosure.

For example, in other examples, the activation treatment and the stabilization treatment may be performed at the same time, for example, the carbon nanotube can be added to the EDC solution and the NHS solution at the same time, so as to change the carboxyl group on the atomic skeleton of the carbon nanotube into the ester group, which can shorten the production time and increase the production rate.

In the example, the EDC solution and the NHS solution respectively used for the activation treatment and the stabilization treatment are not connected to the carbon nanotube or the polypeptide as chemical components, but after the carbon nanotube reacts with the polypeptide, the EDC solution and the NHS solution are converted into water-soluble urea derivatives, which can be excreted with the normal metabolism of human body, so that the cytotoxicity is relatively small.

For example, the carbon nanotube performed with the stabilization treatment directly reacts with the polypeptide, so that the carbon nanotube and the polypeptide are bonded by the chemical bonds.

Step S1014: mixing the carbon nanomaterial with the polypeptide.

For example, before mixing the carbon nanomaterial with the polypeptide, the polypeptide is prepared into a solution, which is conducive to even mixing of the polypeptide with the carbon nanomaterial.

For example, in the example, the polypeptide having the osteogenic induction ability is selected, for example, BMP-2 polypeptide is selected. For example, the BMP-2 polypeptide is dissolved in distilled water and is prepared into BMP-2 polypeptide solution with a mass concentration of 2 to 3 mg/ml. After that, the BMP-2 polypeptide solution is mixed with the carbon nanotube performed with the stabilization treatment, for example, mixed with the NHS solution including the carbon nanotube in the stabilization treatment, the mixed solution is shaken for 4 hours to 6 hours, and then the mixed solution is transferred to a dialysis bag for 72 hours to 90 hours, so that the BMP-2 polypeptide reacts with the carbon nanotube completely. For example, the amino group in the BMP-2 polypeptide reacts with the ester group on the atomic skeleton of the carbon nanotube, so that the BMP-2 polypeptide and the carbon nanotube are bonded by an amide bond. Finally, the reaction products in the dialysis bag are freeze-dried, for example, the reaction products are put into a freeze dryer for 24 hours to 30 hours, and then placed in an environment of about −20° C. for standby.

Figure 6:
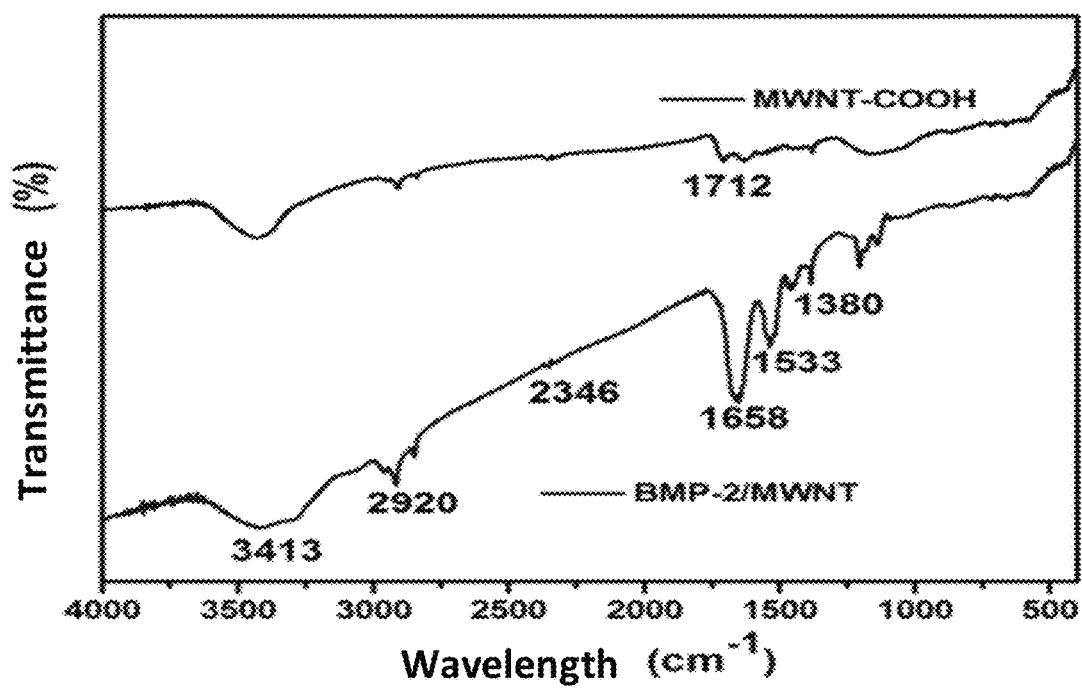
FIG. 6 is an infrared spectrum illustrating a carbon nanomaterial being bonded with a polypeptide by chemical bonds provided by at least one embodiment of the present disclosure.

In the example, the modification process of the carbon nanotube and the principle that the carbon nanotube reacts with the BMP-2 polypeptide can refer to FIG. 4. As illustrated in FIG. 4, after the carbon nanotube (such as MWNT) connected with the carboxyl group (—COOH) is performed with the activation treatment by the EDC solution, the stabilization treatment is performed by the NHS solution to transfer the carboxyl group (—COOH) on the MWNT into the ester group (—COO—), and then the ester group (—COO—) can react with the amino group (—NH$_2$) in the BMP-2 polypeptide to form the amide bond (—CO—NH—), so that the BMP-2 polypeptide and the carbon nanotube (MWNT) are bonded by the amide bond (—CO—NH—). The obtained composite of the BMP-2 polypeptide and the carbon nanotube in the example is tested by infrared spectroscopy, as illustrated in FIG. 6, the infrared spectroscopy shows the infrared spectrum of the carbon nanotube connected with the carboxyl group (MWNT-COOH), and the infrared spectrum of the polypeptide and the carbon nanotube (BMP-2/MWNT) being bonded by the chemical bonds. It can be seen from FIG. 4, there is an obvious absorption peak of the amide bond in the infrared spectrum (BMP-2/MWNT) of the peptide and the carbon nanotube being bonded by the chemical bound. In addition, in the fluorescence test, the BMP-2 polypeptide is labeled with fluorescein, and it is found that green fluorescence appears on the surface of the composite of the polypeptide and carbon nanotube being bonded by the chemical bonds. The above test result indicates that the BMP-2 polypeptide has been bonded with the carbon nanotube by the chemical bonds.

In step S102, the carbon nanomaterial and the polypeptide bonded by the chemical bonds is mixed with the base material.

Figure 5:
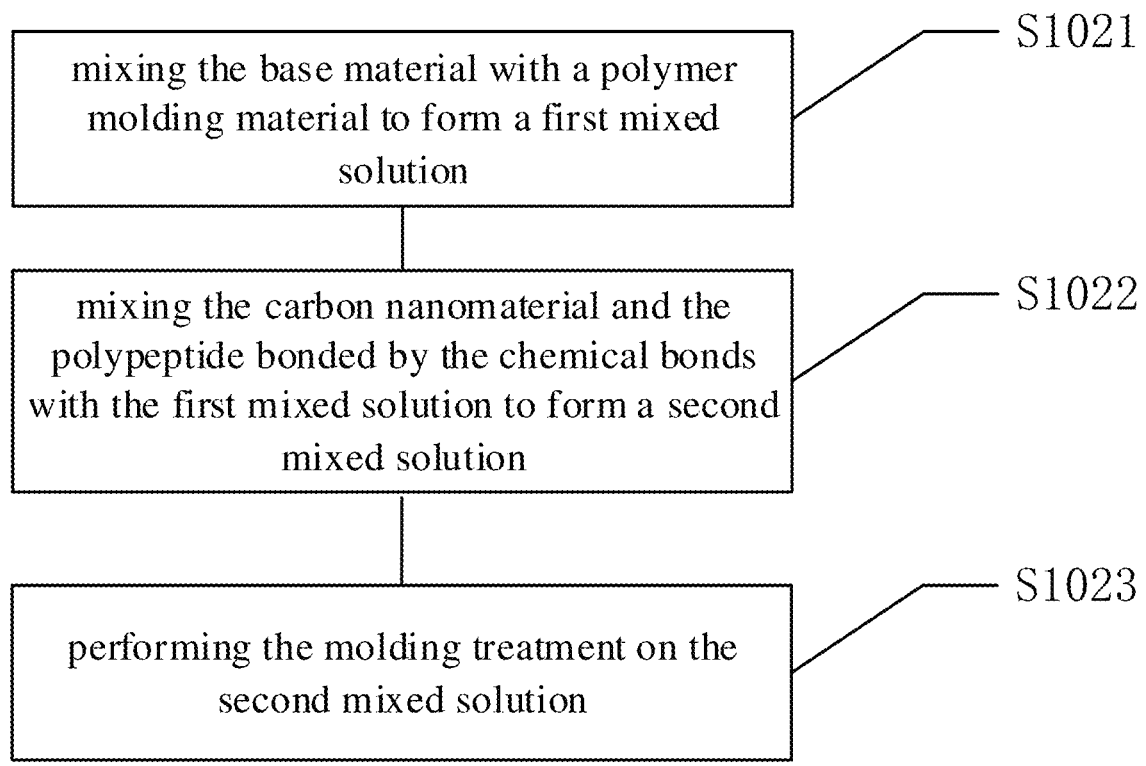
FIG. 5 is a flow chart of still another preparation method of a bone repair material provided by at least one embodiment of the present disclosure.

For example, in the embodiment, as illustrated in FIG. 5, the carbon nanomaterial and the polypeptide bonded by the chemical bonds may be mixed with the base material and a molding treatment may be performed, for example, the process includes steps S1021 to S1023.

Step S1021: mixing the base material with a polymer molding material to form a first mixed solution.

For example, the base material comprises one or more selected from the group consisting of hydroxyapatite (HAP), tricalcium phosphate, and bioglass. For example, in an example, the base material is hydroxyapatite, such as nano hydroxyapatite.

For example, in order to improve the formability of the bone repair material, the polymer molding material can be added to the bone repair material. For example, the base material is mixed with the polymer molding material to form the first mixed solution firstly. For example, the polymer molding material comprises one or more selected from the group consisting of polylactic acid, polycaprolactone, poly (lactic-co-glycolic acid), polyglycolic acid and collagen.

For example, in an example, the polymer molding material uses the polylactic acid (PLA). For example, the poly (L-lactic acid) having a molecular weight in a range of 20000 to 40000 is used. For example, the poly(L-lactic acid) having a molecular weight of 30000 is used.

For example, a solvent for preparing the first mixed solution comprises one or more selected from the group consisting of 1,4-dioxane, dichloromethane and trichloromethane. For example, in an example, the polyl-lactic acid having the molecular weight of 30000 and the nano hydroxyapatite with a mass ratio of (4 to 6):3 are dissolved in the 1,4-dioxane to form the first mixed solution. For example, an overall volume ratio of the poly(L-lactic acid) and the nano hydroxyapatite to the first mixed solution is about 1:3, and then the first mixed solution is ultrasonic treated for 1 hour to 2 hours to make the solution uniform.

Step S1022: mixing the carbon nanomaterial and the polypeptide bonded by the chemical bonds with the first mixed solution to form a second mixed solution.

For example, the carbon nanomaterial and the polypeptide bonded by the chemical bonds which are obtained previously are mixed with the first mixed solution to form the second mixed solution, and the second mixed solution is magnetically stirred, for example, for 4 hours to 5 hours to make the solution uniform.

Step S1023: performing the molding treatment on the second mixed solution.

For example, performing the molding treatment on the second mixed solution by a drying method. For example, in some examples, the molding treatment is performed on the second mixed solution by a freeze-drying method with a mold. For example, the second mixed solution is injected into a mold with a certain shape, and frozen in an environment with a temperature of about −20° C. for about 12 hours, then the frozen mold is transferred to a freeze-drying machine for about 24 hours to 30 hours, and finally a bone repair material with a certain shape is obtained. For example, the mold used in the molding treatment is made of a polymer material, such as polytetrafluoroethylene and so on, and the mold can be formed into any desired shape, which is not limited by the embodiments of the present disclosure.

The bone repair material prepared by the preparation method provided by the present embodiment, the carbon nanomaterial and the polypeptide are bonded by the chemical bonds. Due to a strong binding ability of the chemical bond, the polypeptide can be released slowly, thus the action time of the polypeptide is prolonged and the activity of the bone repair material keeps for a long time. In addition, in the process of preparing the bone repair material, the modified reagents used to modify the carbon nanomaterial, such as the reagents used for the activation treatment and the stabilization treatment, will not be connected with the carbon nanomaterial or the polypeptide as chemical components, but the modified reagents are converted into water-soluble urea derivatives, which can be excreted with the normal metabolism of human body, so the cytotoxicity is relatively small. In addition, the bone repair material is easier to be molded, and the used polymer molding material has a certain mechanical capacity, and its degradation products are normal metabolites of the human body, so there is no toxic side effects. Therefore, the bone repair material provided by the embodiments of the present disclosure has a better comprehensive ability, such as a better osteogenic ability, a better mechanical property, a better molding ability and a better biocompatibility and so on.

The bone repair material provided by the embodiments of the present disclosure can be used in the field of orthopedics as a scaffold material, a filling material and so on, for example, for the treatment of bone defection and so on.

At least one embodiment of the present disclosure further provides a biological composite scaffold, and the biological composite scaffold comprises the bone repair material provided by at least one embodiment of the present disclosure, or the bone repair material prepared by the preparation method provided by at least one embodiment of the present disclosure.

For example, the biological composite scaffold is obtained by performing a molding treatment on the bone repair material. For example, the preparation process of the biological composite scaffold comprises: bonding a carbon nanomaterial with a polypeptide by chemical bonds; then mixing the carbon nanomaterial and the polypeptide bonded by the chemical bonds with a base material, and performing a molding treatment.

Figure 7:
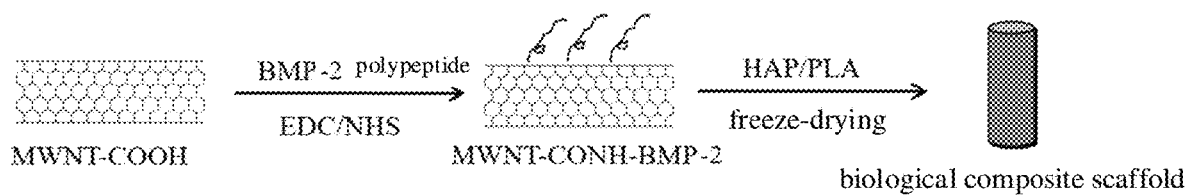
FIG. 7 is a schematic diagram of a preparation process of a biological composite scaffold provided by at least one embodiment of the present disclosure.

FIG. 7 is a schematic diagram of a preparation process of a biological composite scaffold provided by at least one embodiment of the present disclosure. As illustrated in FIG. 7, the carbon nanotube (MWNT-COOH) connected with the carboxyl group (—COOH) is performed with the activation treatment and the stabilization treatment by the EDC solution and the NHS solution respectively, and mixed with the polypeptide (such as the BMP-2 polypeptide), so as to bond the BMP-2 polypeptide with the carbon nanotube connected with the carboxyl group by the amide bond(s) (—CO—NH—). Then, the carbon nanotube and the polypeptide bound by the amide bond(s) (—CO—NH—) are mixed with the base material of hydroxyapatite (HAP) and the molding material of polylactic acid (PLA), after that, the mixed material is injected into a mold with a certain shape and size, and the biological composite scaffold is formed by a freeze-drying method. In this case, the shape and the size of the biological composite scaffold are basically the same as those of the mold. Therefore, in some examples, the shape and the size of the mold can be selected to obtain the biological composite scaffold with a required shape and size.

The biological composite scaffold provided by the embodiments of the present disclosure can be used in the medical field such as the treatment of bone defect.

The following points required to be explained:

(1) The drawings of the embodiments of the present disclosure only relate to the structures related to the embodiments of the present disclosure, and other structures can refer to the general design.

(2) For the sake of clarity, in the drawings used to describe the embodiments of the present disclosure, the thickness of layers or areas is enlarged or reduced, that is, the drawings are not drawn according to the actual scale.

(3) Without conflict, the embodiments of the present disclosure and the features in the embodiments may be combined with each other to obtain new embodiments.

What have been described above are only specific implementations of the present disclosure, the protection scope of the present disclosure is not limited thereto. Any modifications or substitutions easily occur to those skilled in the art within the technical scope of the present disclosure should be within the protection scope of the present disclosure. Therefore, the protection scope of the present disclosure should be based on the protection scope of the claims.

What is claimed is:

1. A bone repair material, comprising: a base material, and a carbon nanomaterial and a polypeptide both mixed with the base material;
    wherein the carbon nanomaterial and the polypeptide are bonded by chemical bonds;
    the bone repair material further comprises a polymer molding material, the carbon nanomaterial comprises a multiple-walled carbon nanotube, the polypeptide comprises a BMP-2 polypeptide, the multiple-walled carbon nanotube and the BMP-2 polypeptide are bonded by amide bonds;
    a total mass fraction of the bone repair material is 100 parts,
    a mass fraction of the base material ranges from 15 parts to 30 parts;
    a mass fraction of the carbon nanomaterial ranges from 6 parts to 10 parts;
    a mass fraction of the polypeptide ranges from 3 parts to 5 parts; and
    a mass fraction of the polymer molding material ranges from 50 parts to 70 parts.

2. The bone repair material according to claim 1, wherein the base material comprises one or more selected from a group consisting of hydroxyapatite, tricalcium phosphate, and bioglass.

3. The bone repair material according to claim 1,
    wherein the polymer molding material comprises one or more selected from a group consisting of polylactic acid, polycaprolactone, poly(lactic-co-glycolic acid), polyglycolic acid and collagen.

4. The bone repair material according to claim 3, wherein the polylactic acid comprises poly(L-lactic acid) having a molecular weight in a range of 20000 to 40000.

5. A biological composite scaffold, comprising: the bone repair material according to claim 1.

6. A preparation method of a bone repair material, comprising:
    bonding a carbon nanomaterial with a polypeptide by chemical bonds; and
    mixing the carbon nanomaterial and the polypeptide bonded by the chemical bonds with a base material and a polymer molding material;
    the carbon nanomaterial comprises a multiple-walled carbon nanotube, the polypeptide comprises a BMP-2 polypeptide, the multiple-walled carbon nanotube and the BMP-2 polypeptide are bonded by amide bonds;
    a total mass fraction of the bone repair material is 100 parts,
    a mass fraction of the base material ranges from 15 parts to 30 parts;
    a mass fraction of the carbon nanomaterial ranges from 6 parts to 10 parts;
    a mass fraction of the polypeptide ranges from 3 parts to 5 parts; and
    a mass fraction of the polymer molding material ranges from 50 parts to 70 parts.

7. The preparation method of the bone repair material according to claim 6, further comprising:
    performing a molding treatment on the carbon nanomaterial, the polypeptide, and the base material that have been mixed.

8. The preparation method of the bone repair material according to claim 7, wherein mixing the carbon nanomaterial and the polypeptide bonded by the chemical bonds with the base material and performing the molding treatment comprise:
    mixing the base material with the polymer molding material to form a first mixed solution,
    mixing the carbon nanomaterial and the polypeptide bonded by the chemical bonds with the first mixed solution to form a second mixed solution, and
    performing the molding treatment on the second mixed solution.

9. The preparation method of the bone repair material according to claim 8, wherein a solvent for preparing the first mixed solution comprises one or more selected from a group consisting of 1,4-dioxane, dichloromethane and trichloromethane.

10. The preparation method of the bone repair material according to claim 9, wherein bonding the carbon nanomaterial with the polypeptide by the chemical bonds further comprises:
    performing a carboxylation treatment on the carbon nanomaterial, and mixing the carbon nanomaterial performed with the carboxylation treatment with the polypeptide, so as to allow the carbon nanomaterial to be bonded with the polypeptide by the chemical bonds.

11. The preparation method of the bone repair material according to claim 10, wherein the carboxylation treatment is an acidification treatment;
    an acid used for the acidification treatment comprises one or more selected from a group consisting of sulfuric acid, nitric acid and hydrogen peroxide.

12. The preparation method of the bone repair material according to claim 10, wherein bonding the carbon nanomaterial with the polypeptide by the chemical bonds further comprises:
    performing an activation treatment on the carbon nanomaterial performed with the carboxylation treatment to activate a carboxyl group of the carbon nanomaterial, and mixing the carbon nanomaterial performed with the activation treatment with the polypeptide, so as to allow the carbon nanomaterial to be bonded with the polypeptide by the chemical bonds.

13. The preparation method of the bone repair material according to claim 12, wherein the activation treatment uses a solution including 1-ethyl-(3-dimethylaminopropyl) carbodiimide hydrochloride.

14. The preparation method of the bone repair material according to claim 12, wherein bonding the carbon nanomaterial with the polypeptide by the chemical bonds further comprises:

performing a stabilization treatment on the carbon nanomaterial performed with the activation treatment to convert the carboxyl group into an ester group, and mixing the carbon nanomaterial performed with the stabilization treatment with the polypeptide, so as to allow the carbon nanomaterial to be bonded with the polypeptide by the chemical bonds.

15. The preparation method of the bone repair material according to claim 14, wherein the stabilization treatment uses a solution including N-hydroxysuccinimide.

16. The preparation method of the bone repair material according to claim 7, wherein the molding treatment is performed by a freeze-drying method.

17. The preparation method of the bone repair material according to claim 10, wherein the carboxylation treatment is an acidification treatment;

the acidification treatment adopts a mixed solution of hydrogen peroxide and sulfuric acid.

* * * * *